United States Patent
O'Rell

[11] 3,944,553
[45] Mar. 16, 1976

[54] BIS QUINOLINE PERI ACIDS
[75] Inventor: Michael K. O'Rell, Redondo Beach, Calif.
[73] Assignee: TRW Inc., Redondo Beach, Calif.
[22] Filed: Feb. 13, 1974
[21] Appl. No.: 442,026

[52] U.S. Cl.... 260/287 P; 260/283 R; 260/283 BZ; 260/287 G
[51] Int. Cl.² ............... C07D 215/50; C07D 491/06
[58] Field of Search....... 260/287 R, 287 G, 283.54, 260/287 P

[56] References Cited
UNITED STATES PATENTS

| | | | |
|---|---|---|---|
| 1,032,123 | 7/1912 | Dohrn | 260/287 R |
| 3,697,400 | 10/1972 | Pang | 260/283.54 |

OTHER PUBLICATIONS

Baloga et al., "J. Phys. Chem." 67, pp. 964–965 (1963).
Morrison and Boyd, "Organic Chemistry," 1967, p. 383.
Fieser and Fieser, "Advanced Organic Chemistry," 1961, p. 391.

*Primary Examiner*—Alton D. Rollins
*Assistant Examiner*—David E. Wheeler
*Attorney, Agent, or Firm*—Daniel T. Anderson; Alan D. Akers; Willie Krawitz

[57] ABSTRACT

Preparation of a novel heterocyclic peri acid is initiated by reacting diaminodimethylbiphenyl with methyl vinyl ketone to produce tetramethyl biquinoline. The substituent methyl groups are oxidized subsequently to produce a tetraacid, or upon dehydration of the tetraacid, a dianhydride. The peri acids of this invention have the following structural formula:

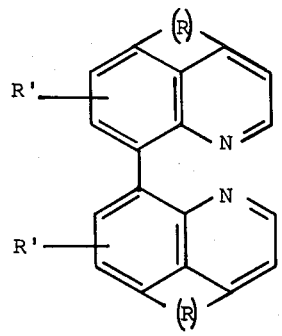

where R may be either

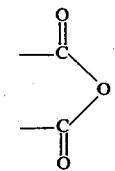

or (—COOH)$_2$
and R' is
—H, —OCH$_3$,

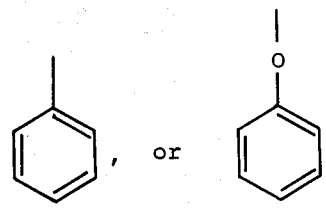

3 Claims, No Drawings

BIS QUINOLINE PERI ACIDS

The invention herein described was made in the course of or under a contract or subcontract thereunder with the Department of Defense.

BACKGROUND OF THE INVENTION

The diaminodimethylbiphenyl starting material used to prepare the heterocyclic peri acids of the present invention were reported by Carlin and Foltz in the *Journal of the American Chemical Society*, Vol. 78, pages 1997 to 2000, May 5, 1956. Carlin et al prepared the diaminodimethylbiphenyl by reacting aminonitrotoluene with potassium iodide in the presence of sodium nitrite to produce iodonitrotoluene. The iodonitrotoluene was heated in the presence of copper powder forming dinitrodimethylbiphenyl by an Ullmann coupling reaction. Exposure of the dinitrodimethylbiphenyl to hydrogen in the presence of a Raney nickel catalyst hydrogenated the nitro substituents to amino substituents thereby forming diaminodimethylbiphenyl. The reaction mechanism is illustrated as follows:

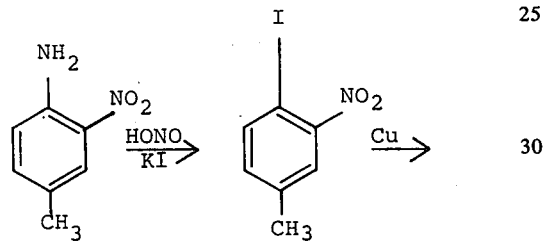

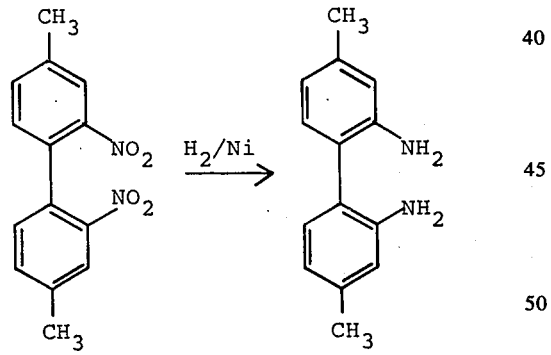

Biquinoline compounds of the present invention may be used in high performance heterocyclic ladder polymers. Examples of polymers similar to those in which these biquinoline compounds may be used have been reported in the *Journal of Polymer Science*, Vol. 6, pages 1777 to 1793, (1968) and Vol. 8, pages 2079 to 2089, (1970).

SUMMARY OF THE INVENTION

Tetracarboxybiquinoline compounds of the present invention are prepared by reacting methyl vinyl ketone with 2,2'-diamino-4,4'-dimethylbiphenyl to produce 4,4',5,5'-tetramethyl-8,8'-biquinoline. The tetramethyl groups on the biquinoline molecule are oxidized by aqueous dichromate to produce 4,4',5,5'-tetracarboxy-8,8'-biquinoline. The reaction may be illustrated as follows:

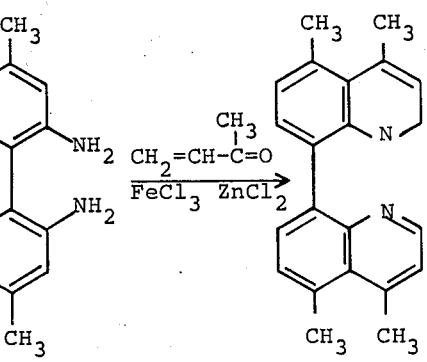

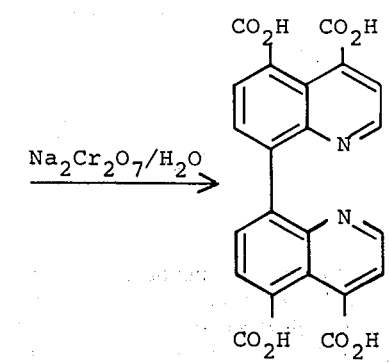

Dehydration of the tetraacid groups will yield the corresponding dianhydride having the structure:

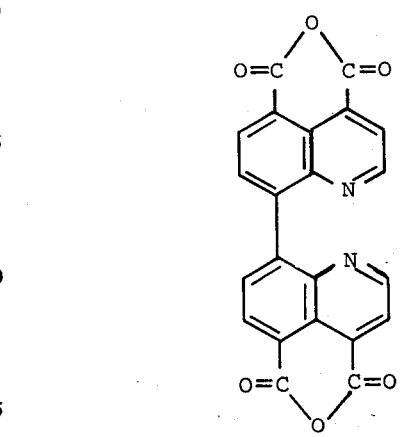

DESCRIPTION OF THE PREFERRED EMBODIMENTS

Heterocyclic peri acids may be prepared by reacting two moles of methyl vinyl ketone per mole of diaminodimethylbiphenyl in the presence of an oxidizing agent and a condensing agent to produce a tetramethylbiquinoline condensation product. Acid groups are formed at the methyl substituents upon oxidation with a dichromate salt. The reaction may be illustrated according to the following:

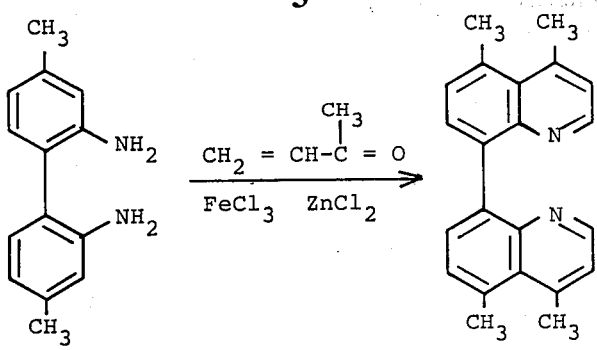

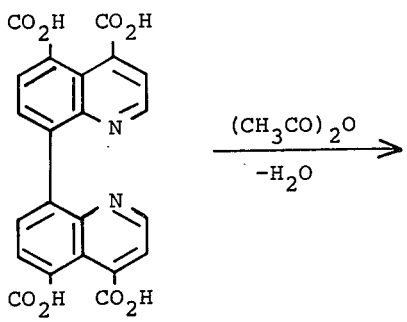

Dehydration to the corresponding dianhydride form is accomplished by reaction with an organic anhydride, such as acetic anhydride or thermally. Conversion to the corresponding dianhydride further purifies the biquinoline compound by selectively dissolving the dianhydride so as to remove it from the inorganic reactants. This reaction is illustrated as follows:

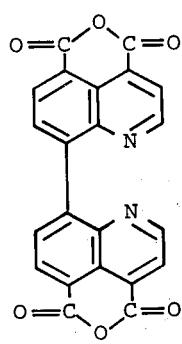

The diaminodimethylbiphenyl from which the present synthesis is initiated is not commercially available, however, the compound can be prepared by the method reported by Carlin and Foltz wherein aminonitrotoluene is reacted with potassium iodide in the presence of nitrous acid to give iodonitrotoluene. Two moles of the iodonitrotoluene are reacted then in the presence of copper powder to produce dinitrodimethylbiphenyl. Subsequent reduction with hydrogen in the presence of a catalyst produces the corresponding amino compound.

The following examples are illustrative of the procedure used to practice this invention. The 2,2'-diamino-4,4'-dimethylbiphenyl was prepared by the procedure reported by Carlin and Foltz as discussed previously.

EXAMPLE I

Preparation of 4,4',5,5'-Tetramethyl-8,8'-biquinoline

To a solution of 110 g (0.386 mole) of diaminodimethylbiphenyl dihydrochloride, 418 g (1.55 mole) of ferric chloride hexahydrate, and 10.2 g (0.075 mole) zinc chloride in 500 ml of 95% ethanol heated to 50°C was added 55.6 g (0.78 mole) of methyl vinyl ketone over a 90 minute period. The solution was refluxed for 2 hours then allowed to stand overnight. Most of the ethanol was removed at reduced pressure and the residue made basic with 25% sodium hydroxide while cooling in an ice bath. The basic solution was evaporated to dryness and the dark residue was extracted 4 times with 400 ml portions of benzene. The extracts were evaporated to dryness to give a dark brown residue.

Extraction of the residue with 150 ml of ethanol resulted in a light brown solid which was sublimed at 250°C, and 0.1 torr pressure to give 20 g (24%) of 4,4',5,5'-tetramethyl-8,8'-biquinoline, mp 290–295°C; ir (KBr) 3010, 2950, 2895, 1905, 1590, 1750, 1500, 1455, 1430, 1390 cm$^{-1}$; nmr (CDCl$_3$) δ 2.92 (s, 6H, 2CH$_3$) 2.95 (s, 6H, 2CH$_3$) 7.07 (d, J = 4Hz, 2H, aromatic) 7.47 (m, 4H, aromatic) 8.50 (d, J = 4Hz, 2H, aromatic). Analytical calculation for C$_{22}$H$_{20}$N$_2$; C, 84.58; H, 6.45; N, 8.97. Found: C, 84.71; H, 6.50; N, 9.30.

EXAMPLE II

Preparation of 4,4',5,5'-Tetracarboxy-8,8'-biquinoline

A mixture of 24.96 g (80 millimole) of tetramethylbiquinoline, 133.5 g (448 millimole) of sodium dichromate dihydrate and 700 ml of water was placed in a stirred Parr pressure apparatus. The mixture was heated and stirred for 5 hours at 250°C. The cooled reaction mixture was filtered to remove chromic oxide, and the green filter cake was washed with 600 ml of hot water. The filtrates were combined and acidified with 6N hydrochloric acid. After cooling overnight, the precipitate which had formed was collected by filtration, washed with water, and dried to give 32.8 g of crude acid. Thin layer chromatography showed the acid to be composed of two components. To complete the oxidation, the acid was dissolved in 300 ml of 10% weight by volume of potassium hydroxide and treated with 200 ml of 5% weight by volume of potassium permanganate. After heating the mixture at 70°C for 45 minutes, the excess permanganate was destroyed with ethanol. The manganese dioxide was removed by filtration and acidification of the filtrate with 6N hydrochloric acid gave a product that contained only one major component by thin-layer chromotography. The acid was redissolved in 400 ml of 10% weight by volume potassium hydroxide. The solution was treated with activated carbon, filtered, and the filtrate acidified with 6N hydrochloric acid. The light tan solid was collected by filtration, washed with water and dried in vacuo to give 30.6 g of tetraacid, ir (KBr) 1700, 1605, 1505, 1365, 1265, 118 cm⁻¹.

EXAMPLE III

Preparation of 4,4',5,5'-Tetracarboxy-8,8'-biquinoline Dianhydride

A mixture of 30.0 g (69 millimole) of tetraacid and 400 ml of acetic anhydride was heated to 120°C. A greenish yellow solution was first obtained then a precipitate formed after approximately 20 minutes of heating. The mixture was heated for a total of 2 hours, cooled, and the yellow precipitate was collected by filtration, washed with ether, and dried to give 19.5 g of crude dianhydride.

A sample of the crude dianhydride was recrystallized from O-dichlorobenzene; m; 362° to 366°C; ir (KBr) 1785, 1735, 1585, 1300, 1215, 1000 cm⁻¹; nmr (DMSO-d₆) δ 8.32 (d, 2H, J = 7.5 Hz, aromatic) 8.35 (d, 2H, J = 4 Hz, aromatic) 8.75 (d, 2H, J = 7.5 Hz) 9.13 (d, 2H, J = 4 Hz, aromatic); mass spectrum, m/e 396, 352, 324, 280, 252. Analytical calculation for $C_{22}H_8N_2O_6$: C, 66.67; H, 2.03; N, 7.07. Found: C, 66.59; H, 2.28; N, 6.88.

I claim:

1. A compound having the structure:

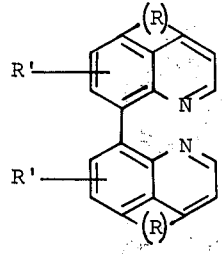

where R is selected from the group consisting of

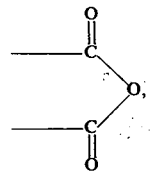

and (—COOH)₂ and R' is selected from the group consisting of —H,

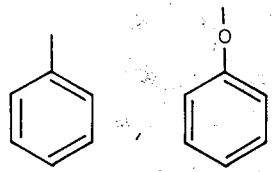

and —OCH₃.

2. A process for the preparation of a compound having the structure:

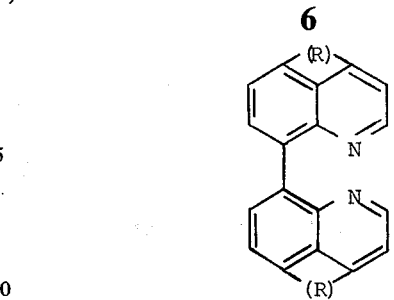

where R is selected from the group consisting of:

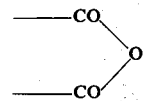

and (—COOH)₂ wherein:

A. an aminonitrotoluene is reacted with potassium iodide to produce a corresponding halonitrotoluene;
B. heating said halonitrotoluene in the presence of powdered copper to produce a corresponding dimethyldinitrobiphenyl;
C. hydrogenating said dimethyldinitrobiphenyl in the presence of a Raney nickel catalyst to produce a corresponding diamino dimethylbiphenyl;
D. reacting said diamino dimethylbiphenyl with methyl vinyl ketone in the presence of inorganic metal chlorides selected from the group consisting of ferric chloride and zinc chloride to yield tetramethylbiquinoline;
E. reacting tetramethylbiquinoline with aqueous dichromate to produce the corresponding tetracarboxybiquinoline; and
F. dehydrating said tetracarboxybiguinoline to the corresponding tetracarboxybiquinoline dianhydride by heating or using a dehydrating agent selected from the group of acetic anhydride wherein each of the above steps includes isolation of the product of each step.

3. A process for the preparation of a compound having the structure:

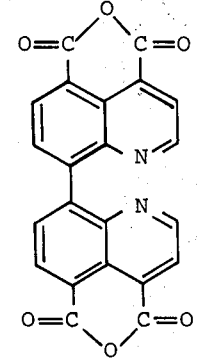

comprising the steps of reacting stoichiometric amounts according to the following:

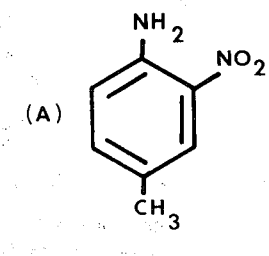 + KI $\xrightarrow{NaNO_2}$ 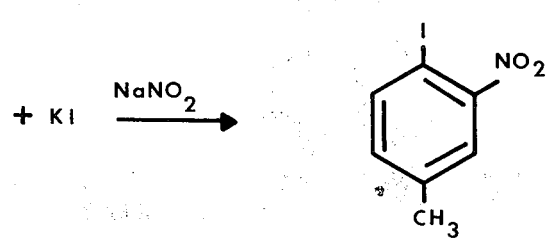

continued:
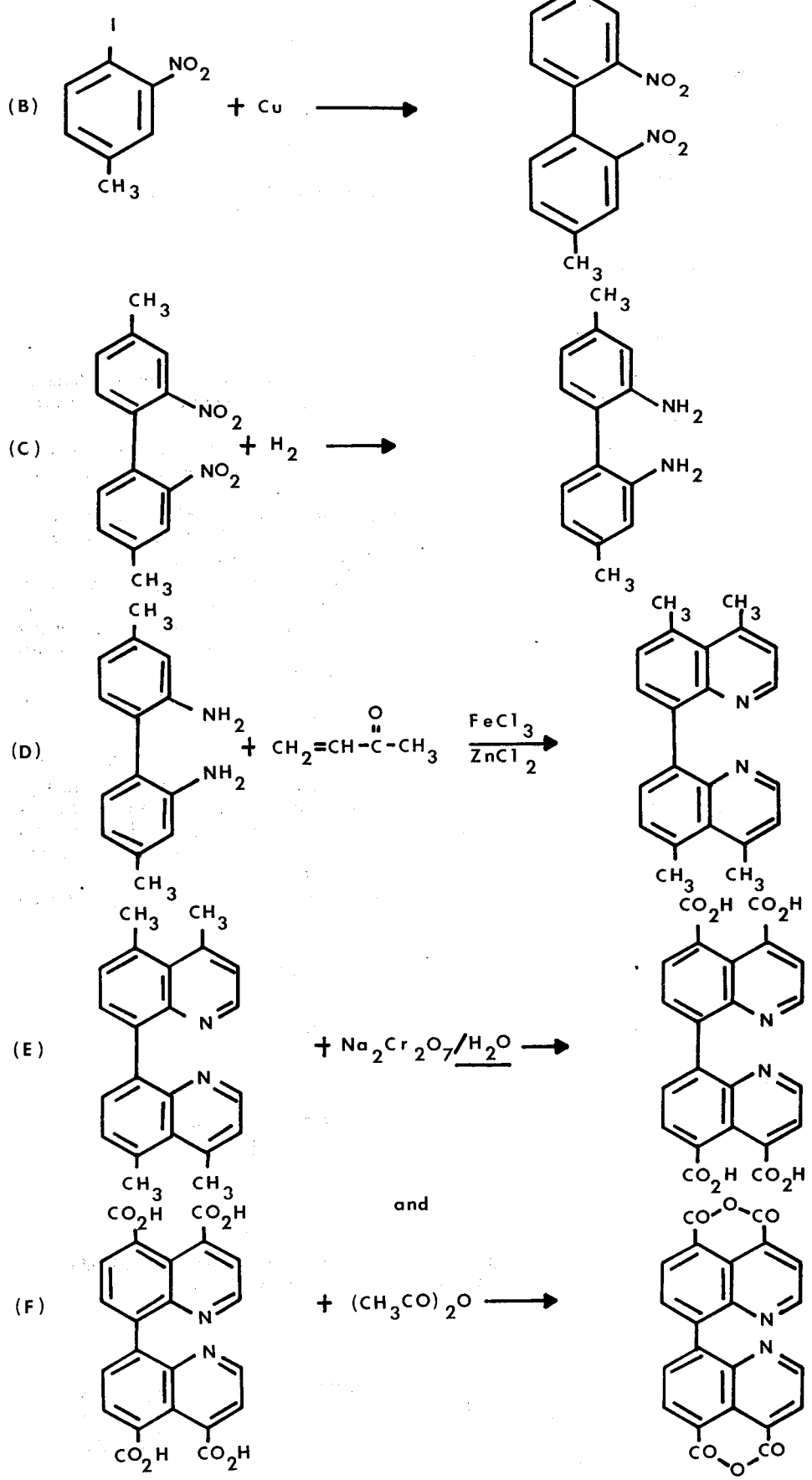
wherein each of the above steps includes isolation of the product of each step.